United States Patent
Horiuchi

(10) Patent No.: US 10,307,130 B2
(45) Date of Patent: Jun. 4, 2019

(54) DOSE CALCULATION APPARATUS, DOSE MANAGEMENT SYSTEM, METHOD FOR CONTROLLING THESE APPARATUS AND SYSTEM, AND RECORDING MEDIUM

(71) Applicant: CANON KABUSHIKI KAISHA, Tokyo (JP)

(72) Inventor: Tetsuya Horiuchi, Tsurugashima (JP)

(73) Assignee: Canon Kabushiki Kaisha, Tokyo (JP)

(*) Notice: Subject to any disclaimer, the term of this patent is extended or adjusted under 35 U.S.C. 154(b) by 335 days.

(21) Appl. No.: 15/130,234

(22) Filed: Apr. 15, 2016

(65) Prior Publication Data
US 2016/0302758 A1    Oct. 20, 2016

(30) Foreign Application Priority Data

Apr. 16, 2015 (JP) ................. 2015-084493
Apr. 16, 2015 (JP) ................. 2015-084494

(51) Int. Cl.
*A61B 6/00* (2006.01)
*A61B 6/03* (2006.01)

(52) U.S. Cl.
CPC .............. *A61B 6/544* (2013.01); *A61B 6/032* (2013.01); *A61B 6/465* (2013.01)

(58) Field of Classification Search
CPC ................. A61B 6/544; A61B 6/032
See application file for complete search history.

(56) References Cited

U.S. PATENT DOCUMENTS 6,404,844 B1 * 6/2002 Horiuchi ................ A61B 6/032
378/16

FOREIGN PATENT DOCUMENTS

| JP | 2004-73397 A | 3/2004 |
| JP | 2006-150033 A | 6/2006 |
| JP | 2008-18044 A | 1/2008 |

* cited by examiner

*Primary Examiner* — Dani Fox
(74) *Attorney, Agent, or Firm* — Canon U.S.A., Inc. IP Division

(57) ABSTRACT

A dose calculation apparatus includes a specifying unit that specifies physical shape information of at least one of a body width and a body thickness of a subject using a ray-sum image generated from a plurality of medical images acquired by imaging the subject with an X-ray apparatus, an acquisition unit that acquires a correction coefficient corresponding to the physical shape information of at least one of the body width and the body thickness specified by the specifying unit from a storage unit configured to store a relationship between the physical shape information and the correction coefficient, and a calculation unit that calculates dose in accordance with a physical shape of the subject based on the correction coefficient acquired by the acquisition unit and a value representing X-ray intensity during taking of medical images.

15 Claims, 17 Drawing Sheets

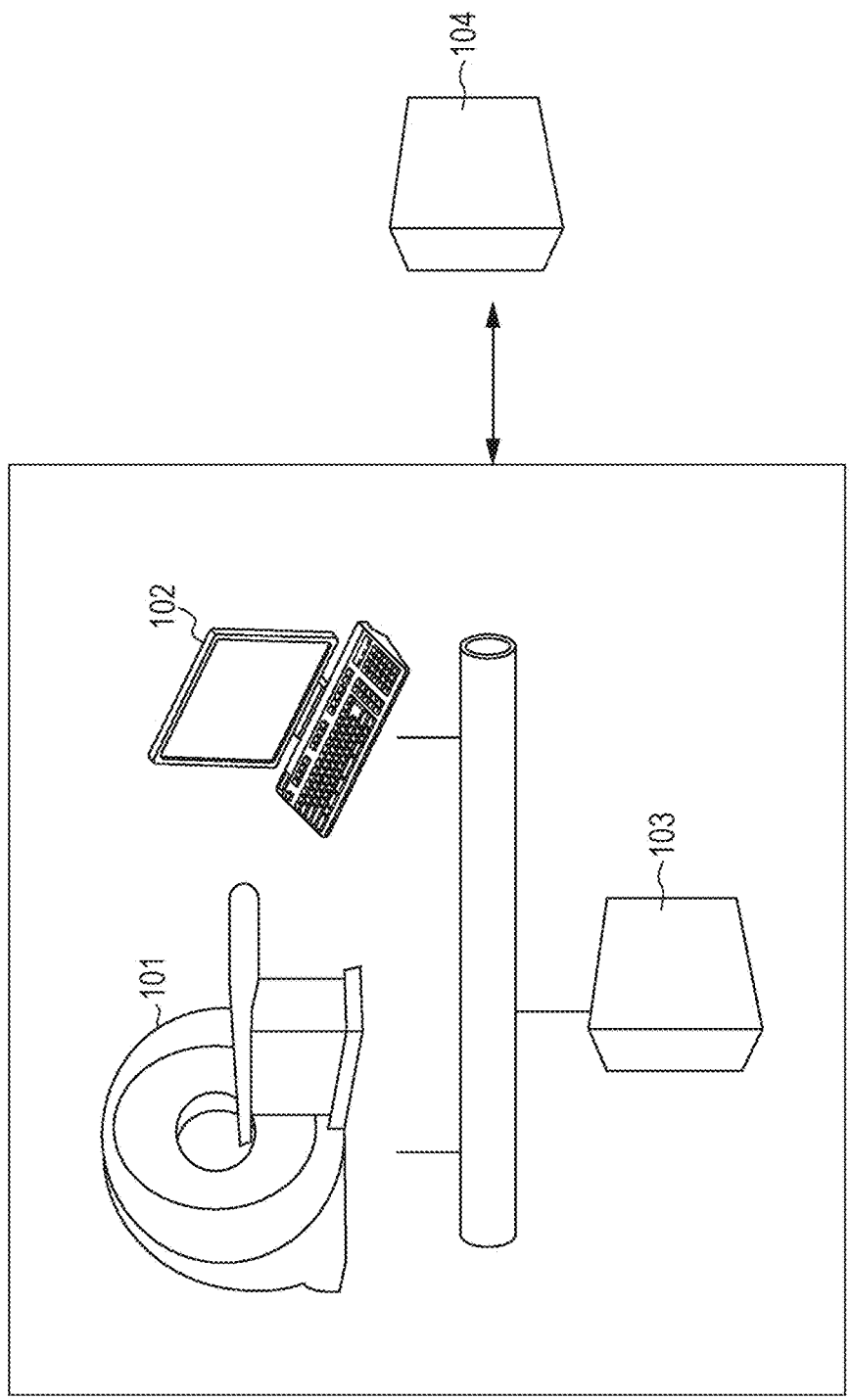

FIG. 4

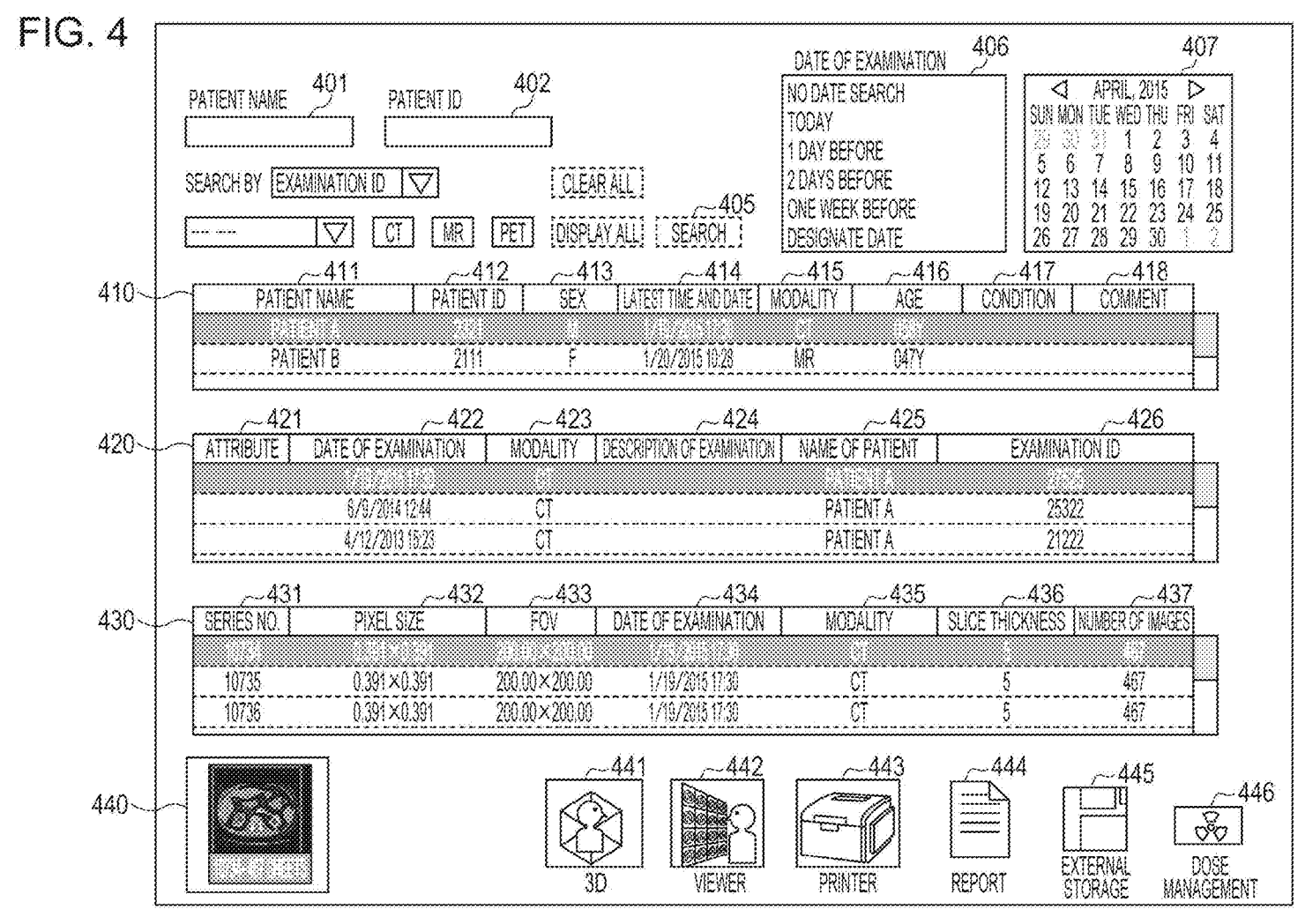

| | PATIENT NAME | 401 | | PATIENT ID | 402 | | | | DATE OF EXAMINATION | 406 | | | APRIL 2015 | 407 |
|---|---|---|---|---|---|---|---|---|---|---|---|---|---|---|

SEARCH BY [EXAMINATION ID ▽] [CT] [MR] [PET] [CLEAR ALL] [DISPLAY ALL] [SEARCH] — 405

- NO DATE SEARCH
- TODAY
- 1 DAY BEFORE
- 2 DAYS BEFORE
- ONE WEEK BEFORE
- DESIGNATE DATE

410 —

| 411 PATIENT NAME | 412 PATIENT ID | 413 SEX | 414 LATEST TIME AND DATE | 415 MODALITY | 416 AGE | 417 CONDITION | 418 COMMENT |
|---|---|---|---|---|---|---|---|
| PATIENT B | 2111 | F | 1/20/2015 10:28 | MR | 047Y | | |

420 —

| 421 ATTRIBUTE | 422 DATE OF EXAMINATION | 423 MODALITY | 424 DESCRIPTION OF EXAMINATION | 425 NAME OF PATIENT | 426 EXAMINATION ID |
|---|---|---|---|---|---|
| | 6/6/2014 12:44 | CT | | PATIENT A | 2322 |
| | 4/12/2013 15:28 | CT | | PATIENT A | 21222 |

430 —

| 431 SERIES NO | 432 PIXEL SIZE | 433 FOV | 434 DATE OF EXAMINATION | 435 MODALITY | 436 SLICE THICKNESS | 437 NUMBER OF IMAGES |
|---|---|---|---|---|---|---|
| 10735 | 0.391 x 0.391 | 280.00 x 280.00 | 7/19/2015 17:30 | CT | 5 | 467 |
| 10736 | 0.391 x 0.391 | 280.00 x 280.00 | 7/19/2015 17:30 | CT | 5 | 467 |

440 —

441 3D  442 VIEWER  443 PRINTER  444 REPORT  445 EXTERNAL STORAGE  446 DOSE MANAGEMENT

FIG. 5

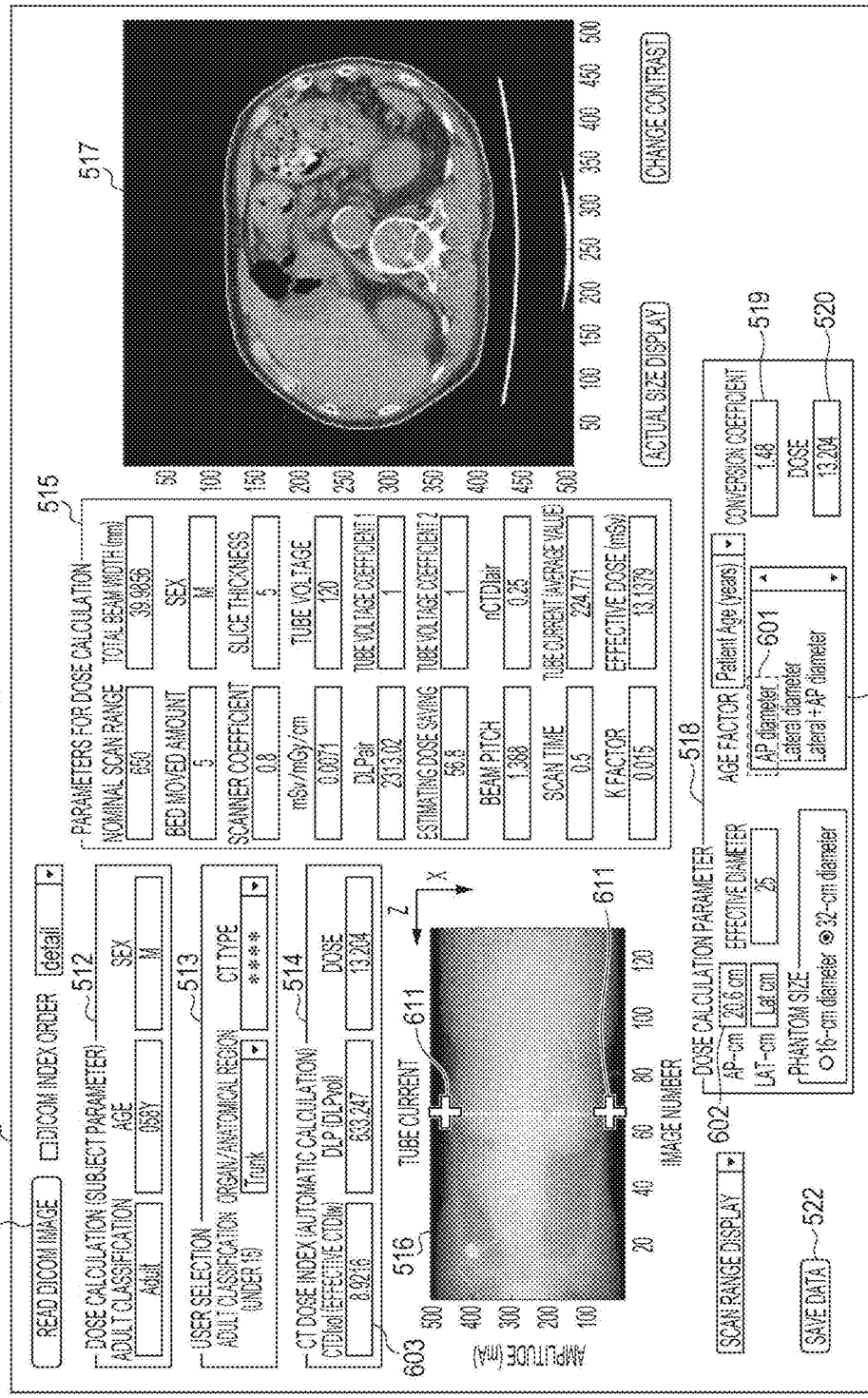

FIG. 9A

| LATERAL+AP(cm) 901 | EFFECTIVE DIAMETER(cm) 902 | CORRECTION COEFFICIENT 903 |
|---|---|---|
| 12 | 5.7 | 1.5 |
| 13 | 6.2 | 1.47 |
| 14 | 6.7 | 1.44 |
| 15 | 7.2 | 1.42 |
| ⋮ | ⋮ | ⋮ |
| 70 | 34.5 | 0.49 |
| 72 | 35.5 | 0.48 |
| 74 | 63.5 | 0.47 |
| ⋮ | ⋮ | ⋮ |

FIG. 9B

| LATERAL(cm) 911 | EFFECTIVE DIAMETER(cm) 912 | CORRECTION COEFFICIENT 913 |
|---|---|---|
| 6 | 8.2 | 1.36 |
| 7 | 8.7 | 1.34 |
| 8 | 9.2 | 1.32 |
| 9 | 9.7 | 1.29 |
| ⋮ | ⋮ | ⋮ |
| 50 | 47.2 | 0.30 |
| 51 | 48.5 | 0.29 |
| 52 | 49.9 | 0.28 |
| ⋮ | ⋮ | ⋮ |

FIG. 9C

| AP(cm) 921 | EFFECTIVE DIAMETER(cm) 922 | CORRECTION COEFFICIENT 923 |
|---|---|---|
| 6 | 5.8 | 1.50 |
| 7 | 7.3 | 1.41 |
| 8 | 8.8 | 1.33 |
| 9 | 10.2 | 1.26 |
| ⋮ | ⋮ | ⋮ |
| 50 | 46.4 | 0.31 |
| 51 | 46.7 | 0.31 |
| 52 | 47.0 | 0.30 |
| ⋮ | ⋮ | ⋮ |

FIG. 9D

| LATERAL+AP (cm) [901] | EFFECTIVE DIAMETER (cm) [902] | CORRECTION COEFFICIENT [903] |
|---|---|---|
| 16 | 7.7 | 1.5 |
| 18 | 8.7 | 1.47 |
| 20 | 9.7 | 1.44 |
| 24 | 10.7 | 1.42 |
| ⋮ | ⋮ | ⋮ |
| 70 | 34.5 | 1.04 |
| 72 | 35.5 | 1.01 |
| 74 | 36.5 | 0.97 |
| ⋮ | ⋮ | ⋮ |

FIG. 9E

| LATERAL (cm) [911] | EFFECTIVE DIAMETER (cm) [912] | CORRECTION COEFFICIENT [913] |
|---|---|---|
| 8 | 9.2 | 2.65 |
| 9 | 9.7 | 2.60 |
| 10 | 10.2 | 2.55 |
| 11 | 10.7 | 2.50 |
| ⋮ | ⋮ | ⋮ |
| 20 | 16.4 | 2.03 |
| 21 | 17.2 | 1.97 |
| 22 | 17.9 | 1.92 |
| ⋮ | ⋮ | ⋮ |

FIG. 9F

| AP (cm) [921] | EFFECTIVE DIAMETER (cm) [922] | CORRECTION COEFFICIENT [923] |
|---|---|---|
| 8 | 8.8 | 2.68 |
| 9 | 10.2 | 2.55 |
| 10 | 11.6 | 2.42 |
| 11 | 13.0 | 2.30 |
| ⋮ | ⋮ | ⋮ |
| 20 | 24.3 | 1.58 |
| 21 | 25.5 | 1.52 |
| 22 | 26.6 | 1.45 |
| ⋮ | ⋮ | ⋮ |

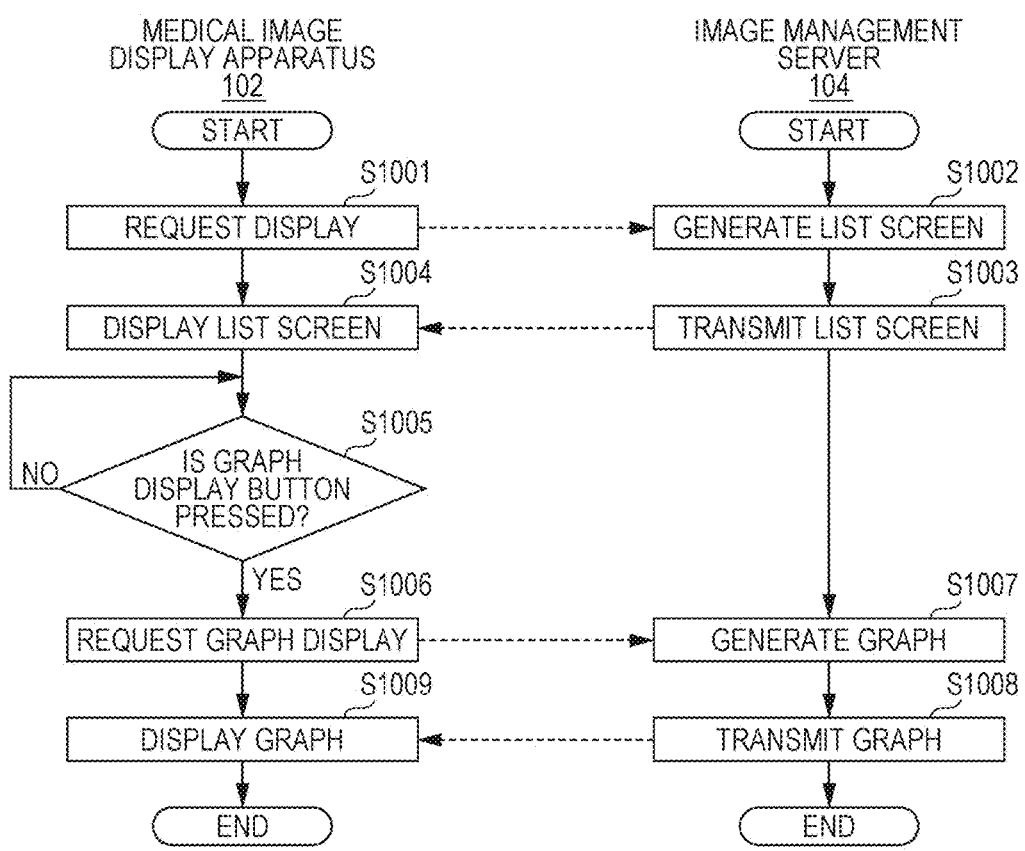

FIG. 11

| | 1102 | 1103 | 1104 | 1105 | 1106 | 1107 | 1108 | 1109 | 1110 | 1111 | 1112 | 1113 | 1114 | 1115 | 1116 | 1117 |
|---|---|---|---|---|---|---|---|---|---|---|---|---|---|---|---|---|
| PATIENT LIST 1101 | | | | | | | | | | | | | | | | |
| SELECT | NO. | DATE OF EXAMINATION | PATIENT ID | PATIENT NAME | SEX | AGE | WEIGHT | BODY PART TO BE IMAGED | NUMBER OF IMAGES | CTDIvol (mGy) | DLP (mGy*cm) | PHANTOM SIZE | DOSE (mGy) | EFFECTIVE DIAMETER | CONVERSION COEFFICIENT |
| ☐ | 1 | 1/19/2015 | 2321 | PATIENT A | M | 58 | 68 | CHEST | 1 | 8.9 | 633.2 | 32 | 13.20 | 26.00 | 1.48 |
| ☐ | 2 | 1/19/2015 | 3232 | PATIENT C | F | 74 | 60 | CHEST | 2 | 7.0 | 215.0 | 32 | 13.40 | 19.10 | 1.91 |
| ☐ | 3 | 1/19/2015 | 2211 | PATIENT D | F | 32 | 69 | ABDOMEN | 2 | 13.8 | 381.0 | 32 | 23.30 | 22.00 | 1.69 |
| ☐ | 4 | 1/19/2015 | 2194 | PATIENT E | M | 58 | 87 | ABDOMEN | 1 | 32.0 | 1271.0 | 16 | — | — | — |
| ☐ | 5 | 1/19/2015 | 2980 | PATIENT F | F | 34 | 53 | ABDOMEN | 2 | 15.6 | 338.0 | 32 | 35.90 | 14.90 | 2.3 |
| ☐ | 6 | 1/19/2015 | 6223 | PATIENT G | F | 34 | 68 | ABDOMEN | 1 | 13.6 | 373 | 32 | — | — | — |

1118 NEW REGISTER   1119 DELETE   1120 DOWNLOAD   1121 SAVE

1130 GRAPH DISPLAY CONDITIONS
BODY PART TO BE IMAGED: ☐ HEAD  ☒ CHEST  ☒ ABDOMEN
SEX: ☒ FEMALE  ☒ MALE
AGE: ☐ UNDER 15  ☐ 15 OR OLDER
ITEM: ☒ CTDIvol  ☒ DOSE
PERCENTILE DISPLAY ☐

1131 DISPLAY

DOSE CALCULATION APPARATUS, DOSE MANAGEMENT SYSTEM, METHOD FOR CONTROLLING THESE APPARATUS AND SYSTEM, AND RECORDING MEDIUM

BACKGROUND

Technical Field

The present invention relates to a dose calculation apparatus, a dose management system, methods for controlling these apparatus and system, and programs thereof.

Description of the Related Art

In a medical image diagnosis in which imaging is conducted using, for example, an X-ray CT apparatus, a volume computed tomography dose index (CTDIvol) during CT scanning is typically used as an index for managing exposure dose of a subject. In the X-ray CT apparatus, a detector is attached to an acrylic resin-made cylindrical reference phantom (hereafter, "CTDI phantom") upon shipping to detect an X-ray amount, and initial setting for every apparatus is performed based on the detection result. Therefore, the CTDIvol can be output as attendant information of medical image data as values in accordance with imaging conditions, such as an X-ray tube current, during CT scanning, and the CTDIvol can be used as an evaluation index of the dose of the subject.

CTDI phantoms used for the initial setting of the apparatus are provided in two sizes based on the examination parts of the subject: 32 cm in diameter for the trunk and 16 cm in diameter for the head. Reference values acquired based on each phantom are stored in the X-ray CT apparatus, and the CTDIvol calculated based on the reference values in accordance with the examination parts are output as attendant information of the medical image data. Although the CTDIvol output as attendant information of the medical image data may be used as the evaluation index of the dose of the subject, a physical shape of a subject is not considered strictly in the CTDIvol. Therefore, a mechanism for calculating dose in accordance with a physical shape of a subject is required.

As a technique of calculating dose in consideration of a physical shape of a subject, Japanese Patent Laid-Open No. 2004-73397 discloses a method for obtaining a physical shape of a subject from a scanned image of the subject laid on a bed (e.g., an AP scanned image: AP scan projection image), and correcting a CTDIvol to a value in accordance with the physical shape.

However, since the AP scanned image used to obtain the physical shape in Japanese Patent Laid-Open No. 2004-73397 is not taken while rotating a gantry, a distance between a subject 1400 and an X-ray tube 1402, and a distance between the subject 1400 and an X-ray detector 1403 change depending on the position of a bed 1301 during imaging as illustrated in FIGS. 24A-1 to 14A-3. An AP scanned image taken in the state of FIG. 14A-1 is illustrated in FIG. 14B-1, an AP scanned image taken in the state of FIG. 14A-2 is illustrated in FIG. 14B-2, and an AP scanned image taken in the state of FIG. 14A-3 is illustrated in FIG. 14B-3. As illustrated in FIGS. 24B-1 to 14B-3, not always the same image is obtained from the same subject. That is, since the body width obtained from the AP scanned image varies depending on the distance from the X-ray tube 1402, dose in accordance with the physical shape of the subject is not reliably calculated by the method disclosed in Japanese Patent Laid-Open No. 2004-73397.

An exemplary method for removing distortion in the AP scanned image is to acquire physical shape information of a subject from a tomographic image taken while rotating a gantry in an X-ray CT apparatus. However, since a plurality of tomographic images are taken in recent CT scanning, in order to calculate dose from a plurality of tomographic images, it is necessary to specify one tomographic image and then obtain physical shape information from the specified image, which is a quite complicated process.

As another problem, since dose cannot necessarily be calculated whenever X-ray computed tomography examination is conducted, examination information managed by the dose management apparatus can include both information of examination in which dose in accordance with the physical shape of the subject is calculated, and information of examination in which dose in accordance with the physical shape of the subject is not calculated.

SUMMARY

The present invention provides a dose calculation apparatus including: a specifying unit configured to specify physical shape information including at least one of a body width and a body thickness of a subject using a ray-sum image generated from a plurality of medical images; an acquisition unit configured to acquire a correction coefficient corresponding to the physical shape information spaced by the specifying unit from a storage unit configured to store a relationship between the physical shape information and the correction coefficient; and a calculation unit configured to calculate dose in accordance with a physical shape of the subject based on the correction coefficient acquired by the acquisition unit and a value representing X-ray intensity during taking of medical images.

The present invention also provides a dose management system including: a dose management apparatus; and a dose calculation apparatus, wherein the dose management apparatus includes: a management unit, configured to manage examination information including a ray-sum image generated from a plurality of medical images acquired by imaging a subject with an X-ray apparatus; and a generation unit configured to generate a list screen about examination information managed by the management unit on which whether dose calculated using physical shape information of the subject specified based on the ray-sum image is included is identifiable a system in which a dose calculation apparatus and a dose management apparatus are connected via a network, wherein the dose management apparatus includes: a management unit configured to manage examination information including a ray-sum image generated from a plurality of medical images acquired by imaging a subject with an X-ray apparatus; and a generation unit configured to generate a list screen about examination information managed by the management unit on which whether dose calculated using physical shape information of the subject specified based on the ray-sum image is included is identifiable.

Further features of the present invention will become apparent from the following description of exemplary embodiments with reference to the attached drawings.

BRIEF DESCRIPTION OF THE DRAWINGS

FIG. 1 illustrates an exemplary system configuration of a dose management system.

FIG. 4 is an exemplary initial screen of the medical image display apparatus.

FIG. 5 illustrates an exemplary dose management screen.

FIG. 6 illustrates an exemplary dose management screen.

FIGS. 9A to 9F are correction tables illustrating correction coefficients to body widths and body thicknesses of subjects used for the correction of dose depending on the physical shape of the subjects.

FIG. 10 is a flowchart for displaying a dose graph.

FIG. 11 is a list screen displaying doses of patients.

FIGS. 14A-1 to 14B-3 illustrate problems in the related art.

DESCRIPTION OF THE EMBODIMENTS

Hereafter, embodiments of the present invention are described in detail with reference to the drawings.

Figures 1, 14A:
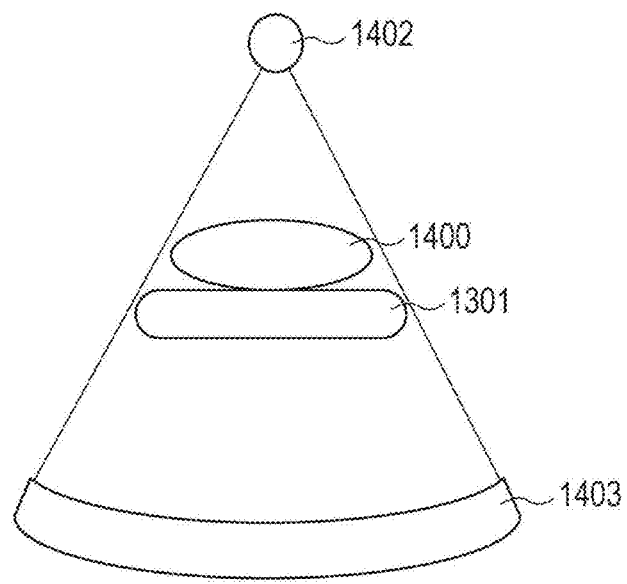

FIG. 1 illustrates a system configuration of a dose management system according to the present embodiment.

In the dose management system of the present invention, a modality 101, such as an X-ray CT apparatus, a medical image display apparatus 102 (a dose calculation apparatus), and an in-hospital image management server 103 (a server apparatus) are connected via an in-hospital network, such as a local area network (LAN) and a wide area network (WAN), for data communication. The in-hospital network may connect also with an outside-hospital image management server 104 (a dose management apparatus) via a network for data communication, and in-hospital images and the like may be stored outside the hospital.

Each terminal configuration of FIG. 1 is illustrative only and various configurations exist depending on the applications and purposes.

Although an X-ray CT apparatus is described as a modality in the present embodiment, the present invention is applicable to any modalities requiring dose management.

The X-ray CT apparatus 101 may transmit taken medical images to the previously set medical image display apparatus 102, the in-hospital image management server 103, or the external image management server 104 for the storage. Medical image data (DICOM image data) taken by the X-ray CT apparatus 101 and transmitted to the server is constituted by attendant information, such as a patient name, a patient ID, patient's sex, a value of an X-ray tube current during imaging by the X-ray CT apparatus, and a CTDIvol (dose information) representing X-ray intensity during taking of the medical image, and image data.

The medical image display apparatus 102 is a workstation that may conduct various types of image processing based on the medical image data (a plurality of pieces of tomographic image data) taken by the X-ray CT apparatus 101. In the present embodiment, dose with the physical shape of the subject reflected therein is calculated in the following manner. A ray-sum image which is an image based on a plurality of tomographic images taken by the X-ray CT apparatus 101 seen from a predetermined direction is generated in the medical image display apparatus 102, the body width or the body thickness, or both of them as an index the physical shape of the subject is acquired on the ray-sum image, a corrected value is acquired from a corrected value table using values in accordance with the physical shape of the subject, and a CTDIvol provided in attendant information of DICOM image data.

The image management server 103 is a server apparatus for storing and managing image taken mainly by an in-hospital modality, and is capable of storing medical images transmitted from a modality and medical images processed in the medical image display apparatus 102. A user can view the medical images in the image management server 103 from a desired location by accessing to the image management server 103 from an in-hospital information processing apparatus (not illustrated).

The image management server 103 is an outside-hospital server apparatus which is capable of storing and managing medical images taken by the in-hospital modality, medical images processed by the medical image display apparatus 102, and the like. The image management server 103 is also capable of receiving requests from a plurality of hospitals, and managing doses of a plurality of hospitals.

Figure 2:
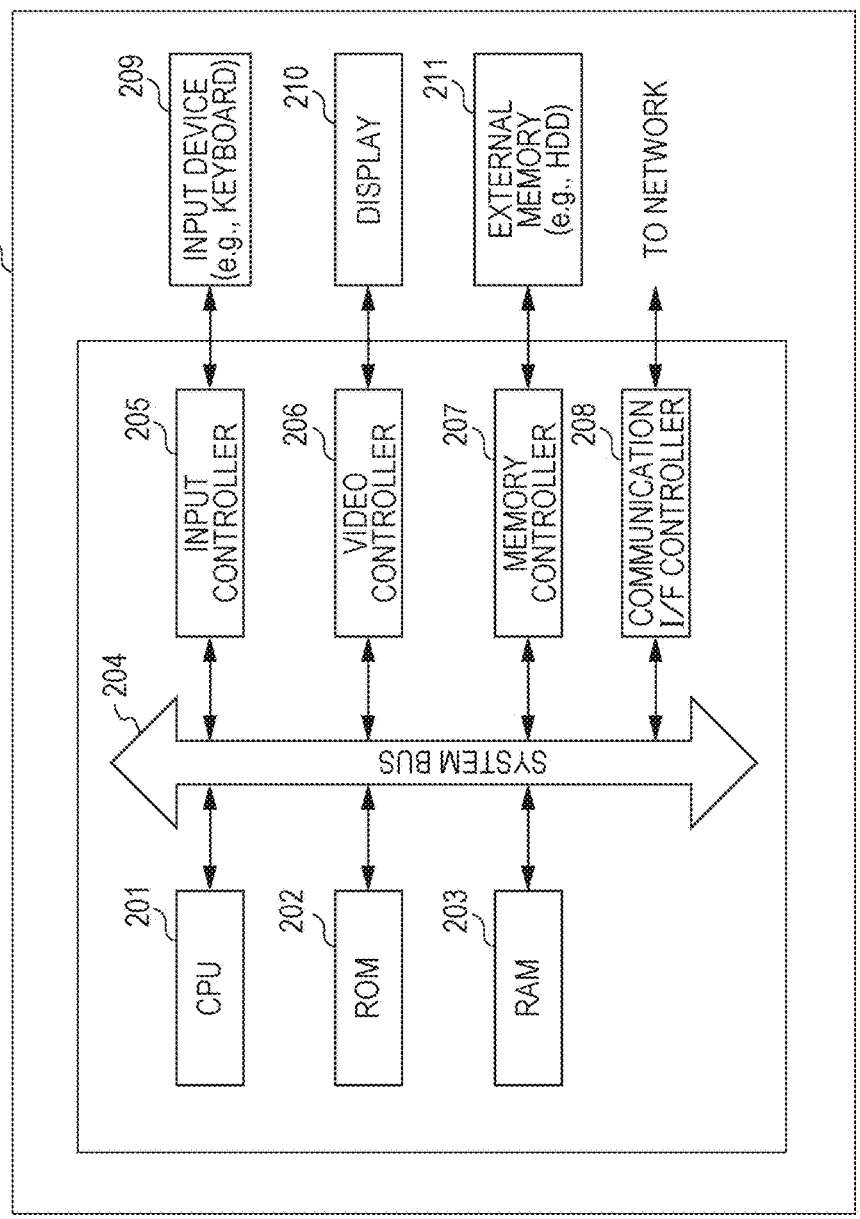
FIG. 2 illustrates exemplary hardware configurations of a medical image display apparatus (an information processing apparatus) and server apparatuses.

FIG. 2 illustrates exemplary hardware configurations of the medical image display apparatus 102, the image management server 103, and the image management server 104.

A CPU 201 collectively controls each device and a controller connected to a system bus 204.

A basic input/output system. (BIOS) which is a control program of the CPU 201, an operating system program (hereafter, "OS"), later-described various programs necessary to perform the functions of the medical image display apparatus 102, the image management server 103, the image management server 104, and the like are stored in ROM 202 or external memory 211 (a storing means). The RAM 203 functions as main memory, a working area, or the like of the CPU 201.

Various operations are executed by the CPU 201 by loading programs and the like to the RAM 203 necessary to execute the processes, and executing the programs.

An input controller 205 controls input from an input device 209, such as a pointing device, like a keyboard and an unillustrated mouse.

A video controller 206 controls display to a display device, such as a display 210. The display device may be CRT and liquid crystal display, but is not limited to the same.

A memory controller 207 controls access to the external memory 211, such as hard disk storing a boot program, browser software, various applications, font data, user files, compilation files, various data, and the like, flexible disk, or card memory connected to a PCMCIA card slot via an adapter.

A communication I/F controller 208 connects to and communicates with an external apparatus via a network, and executes communication and control on a network. For example, Internet communication using TCP/IP may be conducted.

The CPU 201 enables information to be displayed on the display 210 by executing deployment (rasterization) of outline font to, for example, a region for display information in the RAM 203. The CPU 201 enables user instruction to be conducted by, for example, an unillustrated mouse cursor on the display 210.

Various programs used by each terminal of the present invention to execute later-described various processes are recorded in the external memory 211, and are loaded to the RAM 203 as needed to be executed by the CPU 201.

Definition files and various information, tables used by the programs related to the present invention are stored in the external memory 211.

Next, a flow of calculating dose with a physical shape of a subject reflected therein is described with reference to FIGS. 3 to 9F.

Figure 3:
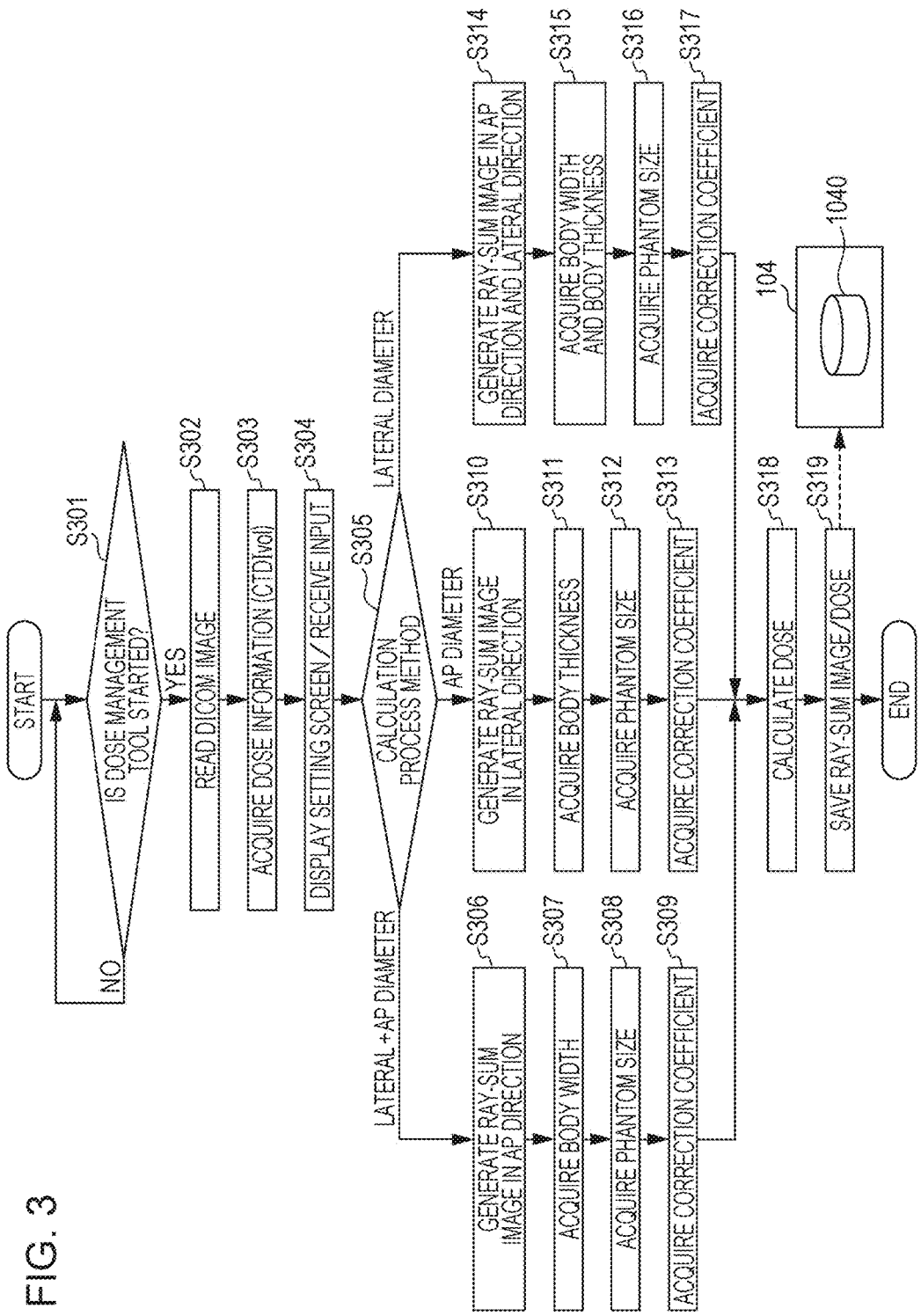
FIG. 3 is a flowchart for calculating dose in accordance with a physical size of a subject.
Figure 5:
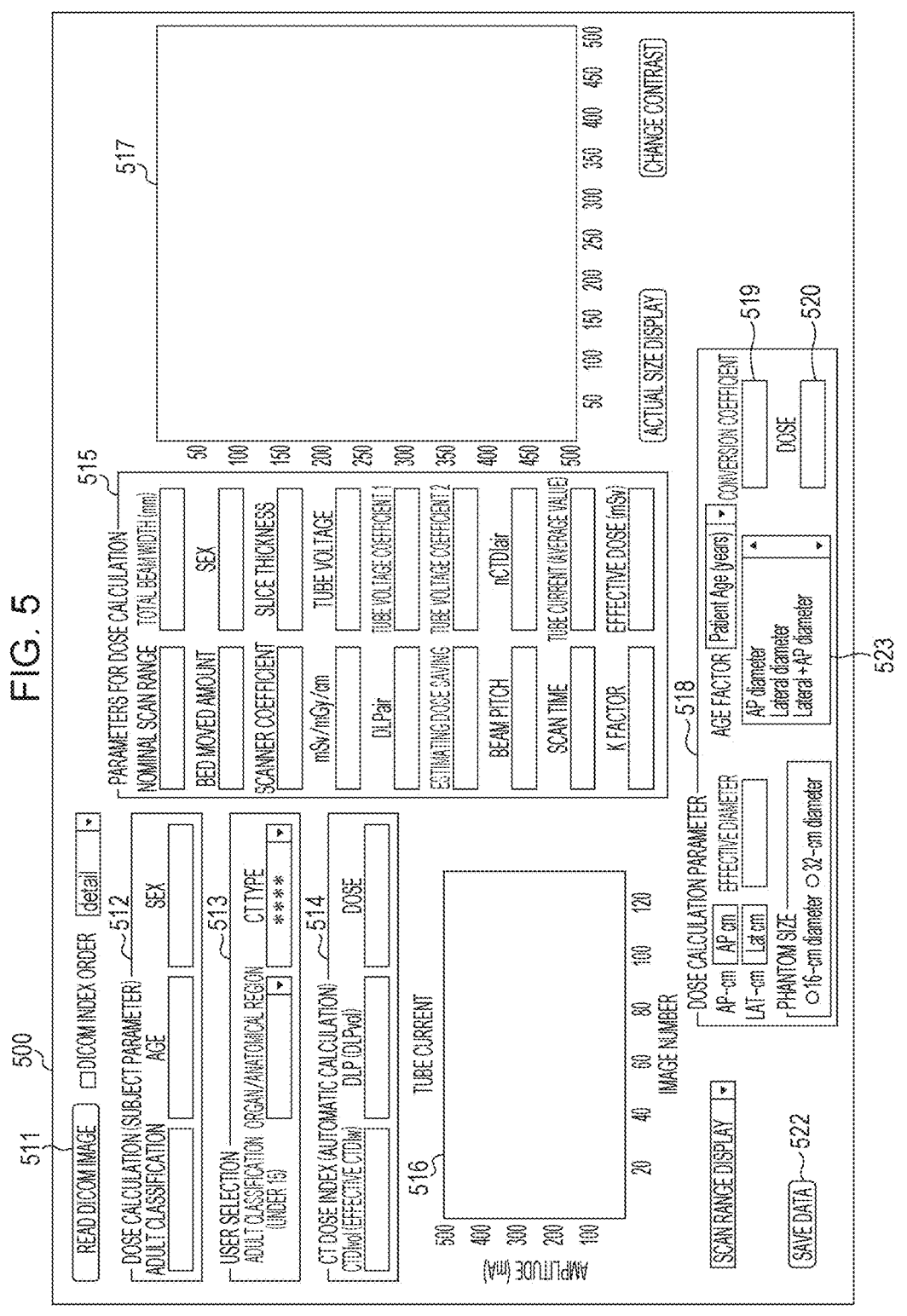
Figure 7A:
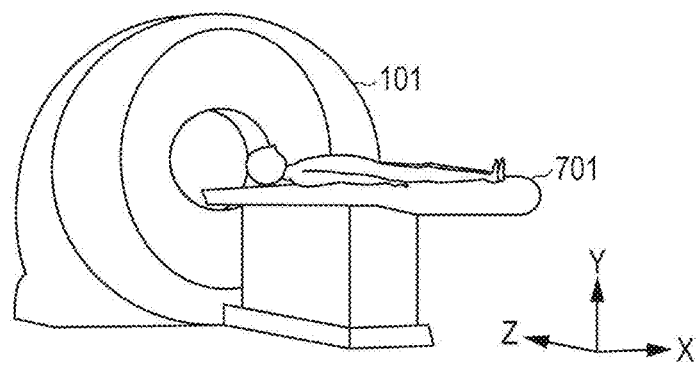
FIGS. 7A to 7C illustrate a process for generating a ray-sum image (in an AP direction).
Figure 7B:
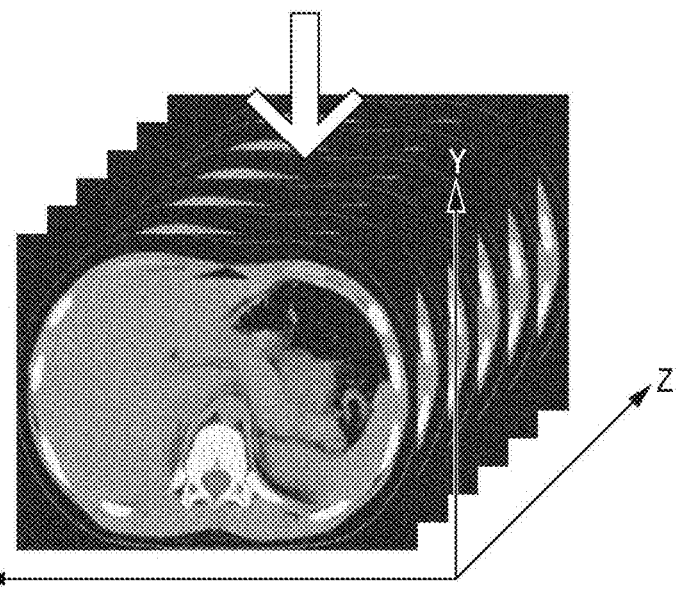
Figure 7C:
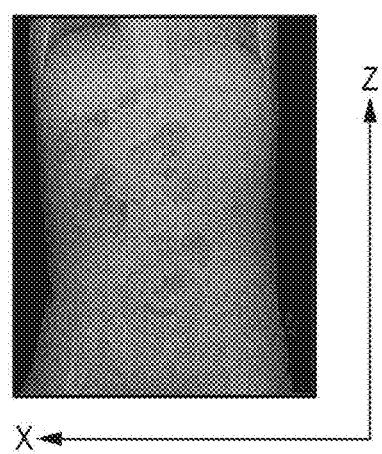
Figure 8A:
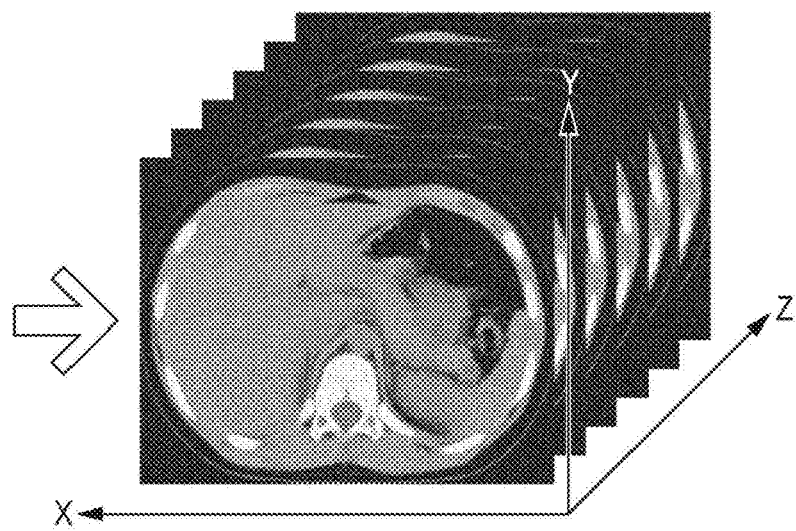
FIGS. 8A and 8B illustrate a process for generating a ray-sum image (in a lateral direction).
Figure 8B:
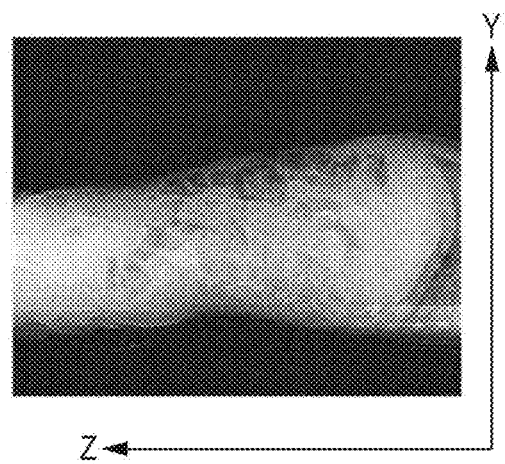

FIG. 3 is a flowchart of a process executed by the medical image display apparatus 102 in the embodiment of the present invention. The process illustrated in the flowchart of FIG. 3 is implemented by the CPU 201 reading and executing the stored control programs. FIG. 4 is an exemplary initial screen of an image processing program of the medical image display apparatus 102. FIG. 5 is an exemplary initial screen of a dose management screen. 500 displayed by the medical image display apparatus 102. FIG. 6 illustrates an exemplary state in which dose with a physical shape of a subject reflected therein is calculated on the dose management screen 500 to be displayed by the medical image display apparatus 102. FIGS. 7A to 7C illustrate a ray-sum image of a subject in a front-back direction. FIGS. 8A and 8B illustrate a ray-sum image of a subject in a left-right direction. FIGS. 9A to 9F are tables each illustrating a relationship among a correction coefficient 903 used to correct a CTDIvol in accordance with the physical shape of the subject previously stored in the storage means of the medical image display apparatus 102, physical shape information (a body width+the body thickness 901, a body thickness 911, a body width 921) of the subject, and an effective diameter 912. FIGS. 9A to 9C are tables each illustrating a correction coefficient used to correct a CTDIvol calculated based on the initial value acquired in a 16-cm phantom in accordance with the physical shape, physical shape information of the subject and an effective diameter. FIGS. 9D to 9F are tables each illustrating a correction coefficient used to correct a CTDIvol calculated based on the initial value acquired in a 32-cm phantom in accordance with the physical shape, physical shape information of the subject and an effective diameter.

In S301 of FIG. 3, the CPU 201 of the medical image display apparatus 102 determines whether a dose management tool has been started. If it is determined that the dose management tool has been started, the process proceeds to S302.

In particular, whether the dose management tool has been started may be determined by whether a dose management button. 446 has been pressed on the initial screen of a medical image processing program provided in the medical image display apparatus 102 illustrated in FIG. 4.

On the initial screen of the medical image display apparatus 102 of FIG. 4, a user can retrieve a medical image stored in the medical image display apparatus 102 or in the image management servers 103 and 104 by pressing a search button 405 with a patient name 401, a patient ID 402, date of examination. 406, a calendar 407, and the like being selected.

The retrieved information is displayed on a list screen 410 as information acquired from the attendant information of the medical image data, such as a patient name 411, a patient ID 412, sex 413, latest time and date 414, a modality 415, age 416, a condition 417, and comments 418.

When the user selects a desired patient on the list screen 410, examination information, such as an attribute of the patient 421, date of examination 422, a modality 423, examination description 424, a patient name 425, and an examination ID 426, is displayed on an examination information list screen 420. If the user selects desired examination information on the examination information list screen 420, series information of the examination information, such as a series No. 431, a pixel size 432, a FOV 433, date of examination 434, a modality 435, a slice thickness 436, and the number of images 437, is displayed on a series information list screen 430. When any of the series information is selected, a thumbnail of the images of the series information or the like may be displayed on a display area 440.

The user may issue instructions on each desired process with desired series information selected, on the series information list screen 430 (or an image among the series of images selected). The desired process may include a 3D drawing button 441 for 3D display based on a plurality of tomographic images taken by the X-ray CT apparatus 101, a viewer button. 442 for viewing the tomographic images, a printer transfer button 443, a report register button. 444 for registering a report, an external storage button 445 for storing the selected images in the image management servers 103 and 104, and a dose management button 446 for performing a dose calculation process. The user may select a desired medical image after pressing a button for starting each desired process.

In S302, the CPU 201 of the medical image display apparatus 102 reads medical image data (DICOM image data) selected by the user. If the series information is selected before the dose management button 446 is pressed, the medical image data of the selected series information is read. If the series information is not selected before the dose management button 446 is pressed, the medical image data may be read by pressing a DICON image reading button 511 on the dose management screen of FIG. 5 and selecting medical image data for which dose is to be calculated.

In S303, the CPU 201 of the medical image display apparatus 102 acquires dose information (CTDIvol) and the like from the medical image data acquired in S302. In particular, when the DICOM image data is read, subject parameters 512, the CTDIvol of a CT dose index 514, parameters 515 for dose calculation, and the like for the calculation of dose illustrated on the dose management screen 500 of FIG. 5 are read from the attendant information of DICOM data.

In S304, the CPU 201 of the medical image display apparatus 102 displays the dose management screen 500 illustrated in FIG. 5 and receives designation of a calculation process method and other input from the user on the dose management screen 500.

In S305, the CPU 201 of the medical image display apparatus 102 determines the calculation process method of the physical shape of the subject designated by the user.

In particular, the calculation process method is designated by the user selecting a method for calculating the physical shape of the subject on the dose management screen of FIG. 5. Physical shape information of the subject may be acquired from the ray-sum image generated based on a plurality of medical images (tomographic images) acquired as DICOM image data. The user may select in a selection column 523 whether the body width acquired from the AP image (the image in the front-back direction) of the subject is used as the physical shape (AP diameter), whether the body thickness acquired from a lateral image (an image in the left-right direction) is used (Lateral diameter), or whether both the body width and the body thickness are used (Lateral+AP diameter).

The user may select setting of a user selection item 513, a phantom size of a dose calculation parameter 518, and the like on the dose management screen 500. If the phantom size may be acquired from the attendant information of the DICOM data, the content of the DICOM data is reflected.

If the dose information, (the CTDIvol) cannot be acquired from the attendant information of the DICOM data, the user may input the dose information on the dose management screen 500.

If it is determined in S305 that the body width obtained from the AP image is used as the physical shape information of the subject (AP diameter is selected), the process proceeds to S306, where the CPU 201 of the medical image display apparatus 102 generates a ray-sum image from a plurality of medical images and displays the generated ray-sum image in a display area 516.

In the X-ray CT apparatus 101, for example, the subject is imaged lying on a bed 701 as illustrated in FIG. 7A, and a plurality of tomographic images are taken as illustrated in FIG. 7B. The ray-sum image is generated based on a value obtained by integrating CT values of the plurality of tomographic images or volume images) in a predetermined direction. FIG. 7O illustrates an exemplary AP image generated in a direction from the front side to the back side of the subject (the AP direction). The thus-generated ray-sum image is displayed in the display area 516 of the dose management screen 500.

In S307, the CPU 201 of the medical image display apparatus 102 acquires body width information of the subject specified by the ray-sum image generated in S306. The body width information may be acquired in the following manner: the body width of the subject at the central position in a body axis direction of the subject in the region examined by the X-ray CT apparatus is automatically acquired from the ray-sum image. Alternatively, two points (611) are designated by the user in the ray-sum image displayed in the display area 516 of FIG. 6, and a distance between the two points may be acquired as the body width information.

In S308, the CPU 201 of the medical image display apparatus 102 acquires the phantom size. If the attendant information of the DICOM data includes data about the phantom size, that data may be referred to regarding the phantom size. If the attendant information of the DICOM data includes no data about the phantom size, the data set by the user via the dose calculation parameter 518 on the dose management screen 500 is acquired.

In S309, the CPU 201 of the medical image display apparatus 102 specifies a table to be used based on the body width information acquired in S307 and the phantom size acquired in S308, and acquires a correction coefficient from the table.

In S318, the CPU 201 of the medical image display apparatus 102 corrects (integrates) the dose information (the CTDIvol) acquired in S303 using the correction coefficient acquired in S309, and calculates corrected dose in accordance with the physical shape of the subject.

In S319, the CPU 201 of the medical image display apparatus 102 stores the ray-sum image generated in S306, the dose calculated in S318, and the like in the storage means. The storage process may be automatically conducted after the dose is calculated, or may be conducted by the user by pressing a data storage button 522 on the dose management screen 500.

The storage means may be a storage means in the medical image display apparatus 102 or a database 1040 in the outside-hospital image management server 104.

Next, a flow of S304 to S309, S318 and S319 is described with reference to an example in which the user selects the AP diameter in the selection column 523 of FIG. 6 (601), sets the distance between the two points on the ray-sum image in the AP direction displayed in the display area 516 to be the body width information, and uses 32 cm as the phantom.

If "20.6 cm" is acquired as the distance (the body width information) between the two points on the ray-sum image displayed in the display area 516, the value is displayed in a column 602 on the dose management screen 500. The medical image on die side on which the body width information is acquired is displayed in a display area 517.

Then FIG. 9F which is the correction table corresponding to the AP image of the 32-cm phantom is specified from the storage means of the medical image display apparatus 102, and the correction coefficient "1.48" and the effective coefficient "25" corresponding to "20.6 cm" are acquired based on die correction table. Even if no body width information exists in the correction table, necessary correction coefficient can be calculated based on two correction coefficient corresponding to two pieces of approximate body width information. Then the acquired correction coefficient "1.48" is displayed on a conversion coefficient column 519, and the effective coefficient "25" is displayed on an effective coefficient column.

If the CTDIvol acquired from the attendant information of the DICOM data is "8.9216" as illustrated in a CT dose index column 603 of FIG. 6, the correction coefficient "1.48" and the CTDIvol "8.9216" are integrated to obtain "13.204" as dose in accordance with the body width.

Although the two points that can be selected in the display area 516 of FIG. 6 are selected at the central position in the body axis direction in the ray-sum image in the present embodiment, these points may be acquired at any positions in the Z direction in the ray-sum image. In the latter case, the dose in accordance with the physical shape may be calculated based on the body width (the physical shape) acquired at this time.

When the user presses the data storage button 522 in this condition, the correction coefficient "1.48" and the dose "13.204" are stored together with the subject information acquired from the DICON image.

As illustrated in this example, dose at an imaging position including a desired organ can be calculated easily by receiving a desired designation part from the user in the ray-sum image and calculating dose in accordance with the physical shape of the corresponding subject.

Returning to FIG. 3, description is continued. If it is determined that the body thickness obtained from the lateral image in S305 of FIG. 3 is used as the physical shape information of the subject (if the Lateral diameter is selected), the process proceeds to S310. In S310, the CPU 201 of the medical image display apparatus 102 generates a ray-sum image from a plurality of medical images and displays the generated ray-sum image in the display area 516. In this case, a lateral image (FIG. 8B) obtained by integrating the CT values along the direction from the left side to the right side of the subject (the lateral direction) as illustrated in FIG. 8A is displayed in the display area 516 on the dose management screen 500.

In S311, the CPU 201 of the medical image display apparatus 102 acquires the body thickness information of the subject specified by the ray-sum image generated in S310. The body thickness information may be acquired automatically from the ray-sum image or, alternatively, two points (611) are designated by the user in the ray-sum image displayed in the display area 516 of FIG. 6, and a distance between the two points may be acquired as the body thickness information.

In S312, the CPU 201 of the medical image display apparatus 102 acquires the phantom size. If the attendant information of the DICOM data includes data about the phantom size, that data may be referred to regarding the phantom size. If the attendant information of the DICOM data includes no data about the phantom size, the data set by the user via the dose calculation parameter 518 on the dose management screen 500 is acquired.

In S313, the CPU 201 of the medical image display apparatus 102 specifies the table to be used based on the body thickness information acquired in S311 and the phantom size acquired in S312, and acquires a correction coefficient from the table.

In S318, the CPU 201 of the medical image display apparatus 102 corrects (integrates) dose information (CTDIvol) acquired in S303 using the correction coefficient acquired in S313, and calculates corrected dose in accordance with the physical shape of the subject.

In S319, the CPU 201 of the medical image display apparatus 102 stores the ray-sum image generated in S310, the dose calculated in S318, and the like in the storage means. The storage process may be automatically conducted after the dose is calculated, or may be conducted by the user by pressing a data storage button 522 on the dose management screen 500.

As described above, also in the case in which the physical shape information of the subject is obtained using the ray-sum image in the lateral direction, dose may be calculated in the same manner as in the case in which the physical shape information of the subject is obtained using the ray-sum image in the AP direction.

If it is determined that the body width and the body thickness obtained from the AP image and the lateral image in S305 are used as the physical shape information of the subject (if Lateral+AP diameter is selected), the process proceeds to S314.

In S314, in the same manner as in S306 and S310, the CPU 201 of the medical image display apparatus 102 generates two ray-sum images in the AP direction and in the lateral direction from a plurality of medical images, and displays the generated ray-sum images in the display area 516.

In S315, the CPU 201 of the medical image display apparatus 102 acquires the body width information and the body thickness information of the subject specified by the ray-sum image generated in S314 in the same manner as in S307 and S311.

In S316, the CPU 201 of the medical image display apparatus 102 acquires the phantom size in the same manner as in S308 and S312.

In S317, in the same manner as in S309 and S313, the CPU 201 of the medical image display apparatus 102 specifies a table to be used based on the body width information acquired in S315 and the phantom size acquired in S316, and acquires a correction coefficient from the table.

In S318, the CPU 201 of the medical image display apparatus 102 corrects (integrates) dose information (CTDIvol) acquired in S303 using the correction coefficient acquired in S317, and calculates corrected dose in accordance with the physical shape of the subject.

In S319, the CPU 201 of the medical image display apparatus 102 stores the ray-sum image generated in S314, the dose calculated in S318, and the like in the storage means. The storage process may be automatically conducted after the dose is calculated, or may be conducted by the user by pressing a data storage button 522 on the dose management screen 500. The ray-sum image, the dose, and the like may be stored in the in-hospital image management server 103 or the outside-hospital image management server 104, instead of the medical image display apparatus 102.

In the present embodiment, as described above with reference to FIGS. 3 to 9F, the CTDIvol which is X-ray intensity during taking of medical images is corrected using the correction coefficient specified using subject information of the subject, which is at least one of the body width and the body thickness specified using the ray-sum image generated from a plurality of medical images.

Figures 1, 14B:
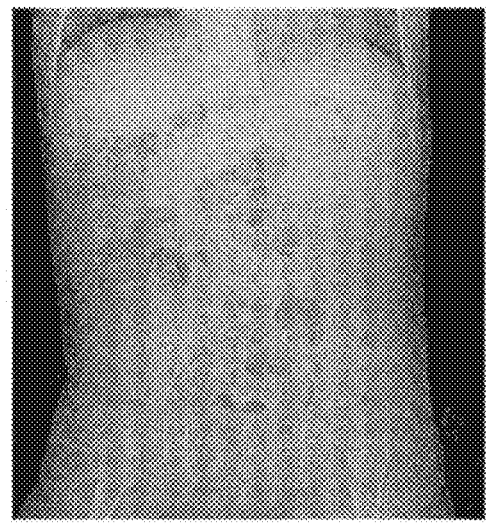
Figures 2, 14A:
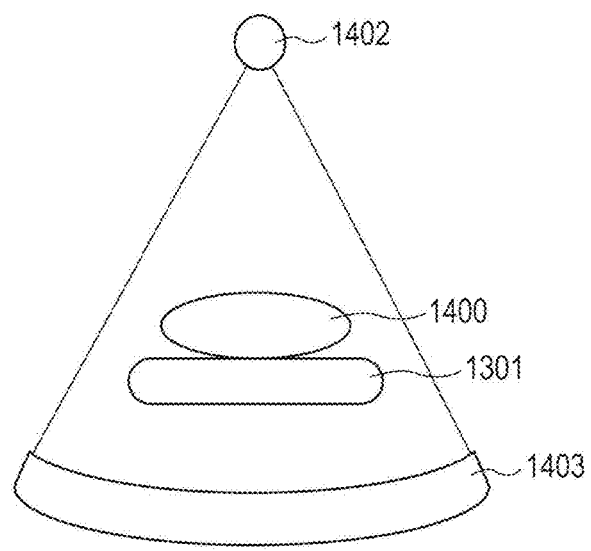
Figures 2, 14B:
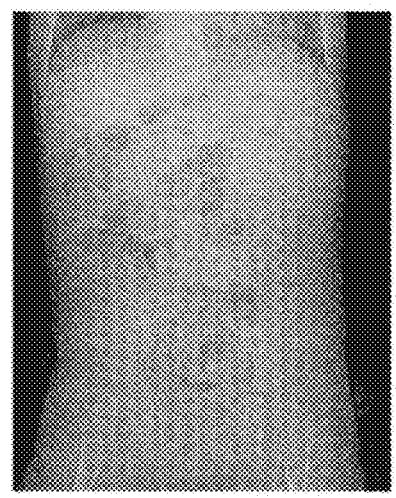
Figures 3, 14A:
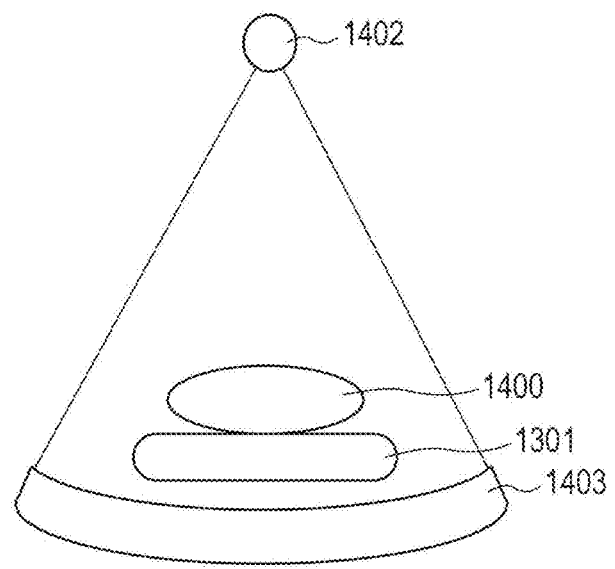
Figures 3, 14B:
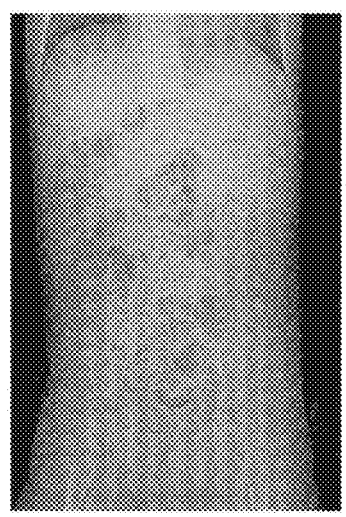

As disclosed in Japanese Patent Laid-Open. No. 2004-73397, a method for obtaining a physical shape of a subject from a scanned image of the subject laid on a bed (e.g., an AP scanned image: AP scan projection image), and correcting a CTDIvol to a value in accordance with the physical shape has been proposed. However, since the related art AP scanned image is not taken while rotating a gantry, a distance between a subject 1400 and an X-ray tube 1402, and a distance between the subject 1400 and an X-ray detector 1403 change depending on the position of a bed 1301 during imaging as illustrated in FIGS. 14A-1 to 14A-3. An AP scanned image taken in the state of FIG. 14A-1 is illustrated, in FIG. 14B-1, an AP scanned image taken in the state of FIG. 14A-2 is illustrated in FIG. 14B-2, and an AP scanned image taken in the state of FIG. 14A-3 is illustrated in FIG. 14B-3. As illustrated in FIGS. 14B-1 to 14B-3, not always the same image is obtained from the same subject. That is, since the body width obtained from the AP scanned image varies depending on the distance from the X-ray tube 1402, dose in accordance with the physical shape of the subject is not reliably calculated by the method disclosed in Japanese Patent Laid-Open No. 2004-73397.

In the present embodiment, since the physical shape is acquired using the ray-sum image, a value in which the physical shape of the subject is reflected more greatly may be calculated than in a case in which the physical shape of the subject from a scanned image taken without rotating the gantry is used as in the related art. Therefore, more reliable dose is acquired in the present invention.

Since the body width and the body thickness of the subject are acquired from the ray-sum image in the present embodiment, time and effort to select, from among a plurality of medical images, a position at which subject information is acquired may be reduced, whereby dose in accordance with the physical shape of the subject is acquired easily.

Although generation of the ray-sum image from a plurality of medical images (tomographic images) and calculation of dose are described as a series of process in the present embodiment, this is not restrictive. If the ray-sum image and a representative value of the CTDIvol which is X-ray intensity during taking of medical images are stored in advance, the physical shape and a representative CTDIvol at desired timing can be acquired and dose in accordance with the physical shape can be calculated. In particular, the user presses the data storage button 522 without designating two points (611) after the generation of the ray-sum image. In this manner, the ray-sum image and the representative value of the CTDIvol which is X-ray intensity during taking of medical images (e.g., the CTDIvol stored as the DICOM image data at the central portion of the image capturing region) are stored without calculating dose in accordance with the physical shape of the subject. Since the ray-sum image is stored, the user can acquire the physical shape information of the subject from the ray-sum image at desired timing, and can acquire dose of which CTDIvol, which is the representative value during taking of medical images, has been corrected in accordance with the physical shape. Therefore, since dose can be calculated even if a plurality of medical images are not stored for the calculation of dose, dose in accordance with the physical shape of the subject can be calculated at desired timing with reduced capacitance of the image management server.

Next, a mechanism for managing dose in accordance with the physical shape of the subject is described with reference to FIGS. 10 to 13B. As illustrated in S319 of FIG. 3, the calculated dose can be managed by the medical image display apparatus 102, the in-hospital image management server 103, or the outside-hospital image management server 104. The dose managed by these management means can be referred to as, for example, a list from the medical image display apparatus 102, an unillustrated information processing apparatus, and the like. Based on the list information, a list and a dose management graph may be generated with reference to the information of the dose managed by the management means.

Here, displaying a dose management graph generated in accordance with a graph generation instruction from the medical image display apparatus 102 based on the dose corresponding to a plurality of subjects managed by the outside-hospital image management server 104 is described.

Figure 12:
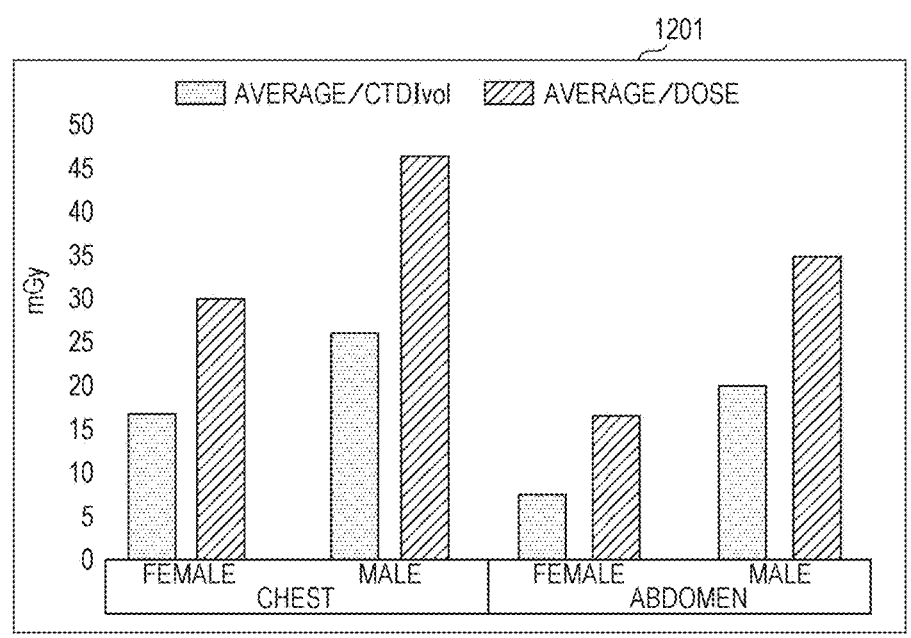
FIG. 12 is an exemplary dose graph.
Figure 13A:
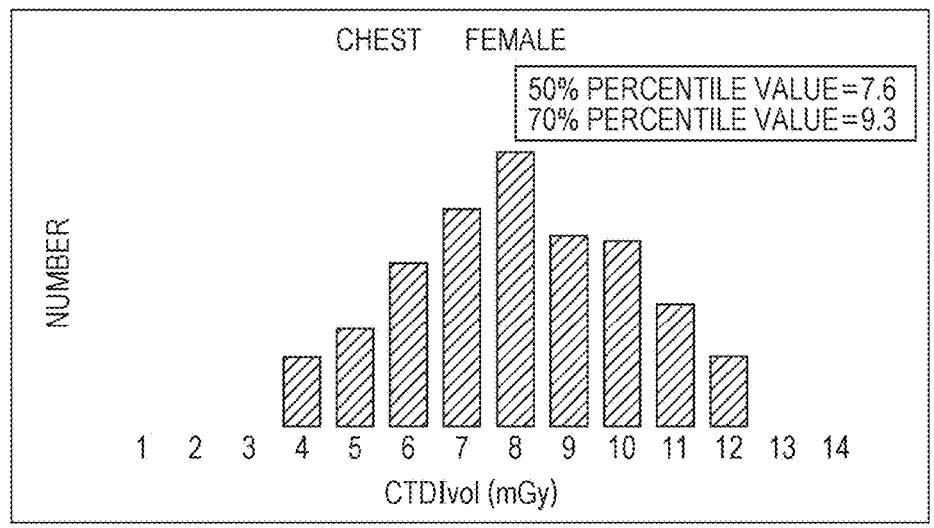
FIGS. 13A and 13B are exemplary dose graphs.
Figure 13B:
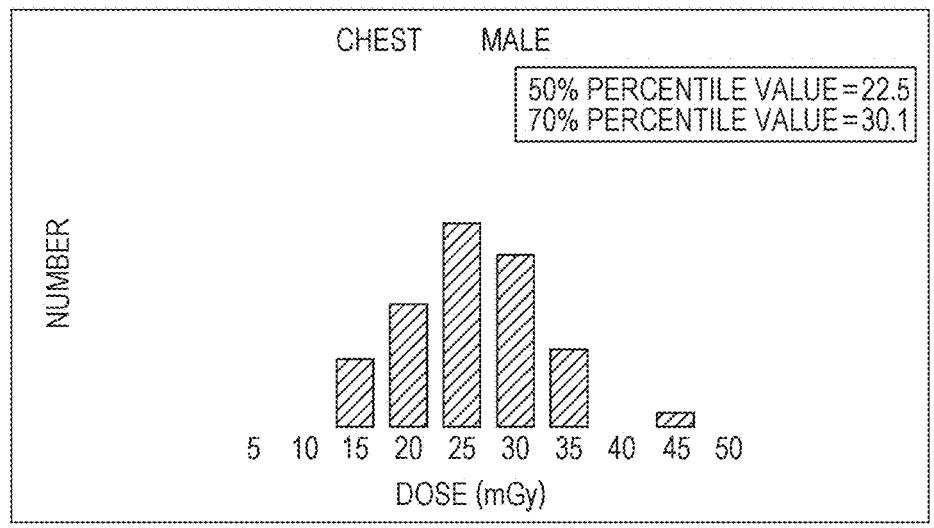

FIG. 10 is a flowchart illustrating a flow of displaying a dose graph. The process of the flowchart of FIG. 10 is implemented by the CPU 201 of the medical image display apparatus 102 and a CPU 201 of the image management server 104 reading and executing stored control programs. FIG. 11 is a list of doses of a plurality of subjects (patients) managed by the image management server 104, and a list screen which is generated by the image management server 104 upon request of the medical image display apparatus 102 and is displayed in the medical image display apparatus 102. The user can instruct display of a dose graph on this screen. Exemplary dose management graphs thus displayed are shown in FIGS. 12, 13A and 13B.

In S1001 of FIG. 10, the CPU 201 of the medical image display apparatus 102 issues a request for displaying listed images to the image management server 104.

In S1002, the CPU 201 of the image management server 104 generates, in response to the display request of the medical image display apparatus 102, a list screen based on a plurality of pieces of X-ray computed tomography examination information managed in the image management server 104. The user can obtain management information, such as a ray-sum image and dose, on the list screen. At the same time, in S1003, a display screen 1101 including the list screen and conditions 1130 for setting graph display conditions is transmitted to the medical image display apparatus 102.

In S1004, the CPU 201 of the medical image display apparatus 102 displays, on the display, the display screen 1101 transmitted from the image management server 104.

An exemplary display screen 1101 is illustrated in FIG. 11. As shown in the display screen 1101 of FIG. 11, selection boxes 1102, management numbers 1103, date of examination acquired from the DICOM data 1104, patient IDs 1105, patient names 1106, sex 1107, age 1108, weight 1109, and body parts to be imaged 1110 are managed in the image management server 104. The number of images 1111 representing the number of stored ray-sum images, CTDIvol 1112 which is X-ray intensity during taking of medical images (representative values of CTDIvol used during calculation of dose or CTDIvol specified when the data storage button 522 is pressed), DLP 1113, and phantom sizes 1114 are also managed in the image management server 104. Doses 1115 calculated after correcting the CTDIvol in accordance with the physical shapes of the subjects, effective diameters 1116 acquired from the correction table, conversion coefficients 1117, and the like are also managed in the image management server 104.

On the list screen, examination information in which data is registered after the dose 1115 is calculated and examination information in which data is registered in a state in which the ray-sum image is generated but no dose 1115 is calculated are displayed as a list in an identifiable manner. In the example of FIG. 11, data of which management numbers 1103 are No. 1, No. 2, No. 3 and No. 5 correspond to examination information in which data is registered after the dose 1115 in accordance with the physical shape of the subject is calculated. Data of which management numbers 1103 are No. 4 and No. 6 correspond to examination information in which data is registered in a state in which the ray-sum image is generated but no dose 1115 is calculated. In this example, the state of the examination information can be determined by the existence of the value of the dose 1115 and the like. Since data is displayed so that the user can determine on the list screen, the user can check easily whether the dose in accordance with the physical shape of the subject has been calculated in the examination information managed by a dose management means.

A new registration button 1118 on the display screen 1101 is used to register information, such as a ray-sum image and the dose 1115, of a new patient without using the dose management screen 500. A deletion button 1119 on the display screen 1101 is used to delete examination information selected in the selection box 1102. A download button 1120 on the display screen 1101 is used to download information, such as the ray-sum image and the dose 1115 managed as a management item of the examination information selected in the selection box 1102. A save button 1121 on the display screen 1101 is used to save the examination information selected in the selection box 1102.

Here, a case in which dose in accordance with the physical shape of the subject is to be registered with respect to the examination of No. 4 or No. 6 in which a ray-sum image has been generated but dose 1115 has not been calculated is described. If the user presses the download button 1120 with No. 4 or No. 6 being selected, the CPU 201 of the medical image display apparatus 102 starts a dose management tool. The CPU 201 of the medical image display apparatus 102 acquires corresponding ray-sum image and representative value of CTDIvol stored in the management server 104. In the same manner as in the flow of the dose calculation described with reference to FIGS. 3 to 9F, at least one piece of subject information, i.e., at least one of the body width and the body thickness, is specified from the ray-sum image, and the CTDIvol is corrected using the specified subject information to calculate dose.

By pressing the data save button 522 on the dose management screen 500, the calculated dose can be saved on the downloaded examination information.

Alternatively, the dose may be saved directly without calculation in the medical image display apparatus 102. As described above, since the ray-sum image is stored, dose can be calculated and stored at desired timing even if a plurality of tomographic images are not stored.

Returning to FIG. 10, description of the graph generation process is continued. In S1005, the CPU 201 of the medical image display apparatus 102 determines whether a graph display button 1131 has been pressed by the user. If it is determined that the graph display button 1131 has been pressed by the user, the CPU 201 of the medical image display apparatus 102 issues a request for displaying a graph to the image management server 104 while presenting the conditions in the condition column 1130 of the graph display conditions in S1006. In particular, a request for displaying a graph corresponding to the items checked in the condition column 1130 when the graph display button 1131 is pressed is issued to the image management server 104.

In S1007, the CPU 201 of the image management server 104 generates a graph in accordance with the conditions designated by the user. Graph templates applied to each condition setting are prepared in advance. A template is selected in accordance with the conditions set in the condition column 1130 and a graph is generated by reflecting the data managed as the dose in the template.

In S1008, the CPU 201 of the image management server 104 transmits the graph generated in S1007 to the medical image display apparatus 102.

In S1009, the CPU 201 of the medical image display apparatus 102 displays the graph transmitted from the image management server 104, and the process completed.

Hereafter, an exemplary graph generated in this manner is described. A case in which the graph display button 1131 is pressed under the conditions that the body part to be imaged: chest, abdomen; and sex: female, male, and item: CTDIvol and dose are selected in the condition column 1130 of FIG. 11 is illustrated in FIG. 12. In this case, a graph in which a template in which chest and abdomen are displayed separately, female and male are displayed separately, and CTDIvol and dose are displayed separately is selected, and managed examination information is plotted is displayed.

If the body part to be imaged: chest; sex: female; the item: CTDIvol are selected and the percentile display is checked in the condition column 1130 illustrated in FIG. 11, the template as illustrated in FIG. 13A is selected and a graph in which the examination information is plotted is displayed.

If the body part to be imaged: chest; sex: male; the item: dose are selected and the percentile display is checked in the condition column 1130 illustrated in FIG. 11, the template as illustrated in FIG. 13B is selected and a graph in which the examination information is plotted is displayed.

If either of the items is not selected in condition column of FIG. 11, a graph cannot be displayed. If neither of them is selected, the graph display button 1131 can be grayed out to become non-selectable.

The user can obtain an index of appropriate dose since a graph in accordance with desired conditions can be displayed based on the thus managed examination information.

The present invention may be embodied as, for example, a system, an apparatus, a method, a program, or a storage medium, and may be applied to a system constituted by a plurality of apparatuses or an apparatus configured by a single device.

The present invention includes supplying a program of software which performs the function of the above embodiments to a system or an apparatus directly or remotely. The present invention also includes performing the function of the above embodiments by an information processing apparatus of the system or the apparatus reading and executing the supplied program code.

Therefore, a program code itself to be installed in the information processing apparatus to perform the function processing of the present invention in the information processing apparatus also embodies the present invention. A computer program itself to perform the function processing of the present invention is also included in the present invention.

The computer program may be an object code, a program executed by an interpreter, script data supplied to an OS, and the like as long as it has a function of a program.

Recording media from which the program is supplied include a flexible disk, hard disk, an optical disc, a magneto-optical disc, an MO, a CD-ROM, a CD-R, a CD-RW, a magnetic tape, a nonvolatile memory card, ROM, and a DVD (a DVD-ROM and a DVD-R).

The program may also be supplied in the following manner: a user accesses an Internet website using a browser of a client computer, and downloads a computer program itself of the present invention, or a compressed file which is to be automatically installed from the website to a recording medium, such as hard disk.

The present invention is implementable by dividing the program code constituting the program of the present invention into a plurality of files, which are downloaded from different websites. That is, a WWW server which causes a plurality of users to download the program files to perform the function processing of the present invention in the information processing apparatus is also included in the present invention.

The present invention is implementable by distributing, to the users, the program of the present invention which is encrypted and stored in a storage medium, such as a CD-ROM, and causing users who satisfy predetermined conditions to download key information to decrypt the program from the website on the Internet, and causing the users to execute the program decrypted by the downloaded key information and install the program in the information processing apparatus.

The functions of the above embodiments are performed when the information processing apparatus executes the read program. The functions of the above embodiments may also be performed by a process performed partly or entirely by, for example, an OS operating on the information processing apparatus in accordance with an instruction of the program.

The program read from the recording medium may be written in memory provided in a function extension board inserted in the information processing apparatus or a function expansion unit connected to the information processing apparatus. The functions of the above embodiments may also be performed by a process performed partly or entirely by a CPU provided in the function extension board or the function expansion unit in accordance with an instruction of the program.

The above embodiments are to be considered as an exemplary form of implementation of the present invention, and the technical scope of the present invention should not be restrictively interpreted. The present invention may be implemented in various forms without departing from the spirit or essential characteristics thereof.

According to one of the embodiments of the present invention, an index of dose in accordance with a physical shape of a subject may be acquired easily by correcting a value representing X-ray intensity during taking of medical images using physical shape information including at least one of a body width and a body thickness of the subject specified using a ray-sum image generated from a plurality of medical images.

According to another embodiment of the present invention, whether dose in accordance with a physical shape of a subject has been calculated in examination information managed by a dose management means can be checked easily by generating a list screen on which whether dose calculated using physical shape information of a subject specified based on a ray-sum image is included is identifiable.

Other Embodiments Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™, a flash memory device, a memory card, and the like.

While the present invention has been described with reference to exemplary embodiments, it is to be understood that the invention is not limited to the disclosed, exemplary embodiments. The scope of the following claims is to be accorded the broadest interpretation so as to encompass all such modifications and equivalent structures and functions.

This application claims the benefit of Japanese Patent Application Nos. 2015-084493 and 2015-084494, filed Apr. 16, 2015, which are hereby incorporated by reference herein in their entirety.

What is claimed is:

1. A dose calculation apparatus comprising:
at least one processor; and
at least one memory storing instructions to be executed by the at least one processor, wherein the at least one processor executes the instructions to function as:
a specifying unit configured to specify physical shape information of at least one of a body width and a body thickness of a subject using a ray-sum image generated from a plurality of medical images acquired by imaging the subject with an X-ray computed tomography (CT) apparatus;
an acquisition unit configured to acquire a correction coefficient corresponding to the physical shape information of at least one of the body width and the body thickness specified by the specifying unit from a storage unit configured to store a relationship between the physical shape information and the correction coefficient; and
a calculation unit configured to calculate dose in accordance with a physical shape of the subject based on the correction coefficient acquired by the acquisition unit and dose information acquired by taking of medical images.

2. The dose calculation apparatus according to claim 1, further comprising a storage unit configured to store the dose calculated by the calculation unit together with the physical shape information.

3. The dose calculation apparatus according to claim 2, wherein the storage unit also stores the ray-sum image used when the specifying unit specifies the physical shape information.

4. The dose calculation apparatus according to claim 1, wherein the ray-sum image used by the specifying unit to specify the physical shape information is at least one of a ray-sum image in a front-back direction of the subject and a ray-sum image in a left-right direction of the subject.

5. The dose calculation apparatus according to claim 1, wherein the specifying unit specifies a length of the subject at the central position in a body axis direction of the subject from the ray-sum image.

6. The dose calculation apparatus according to claim 1, wherein the specifying unit receives designation of positions of two points from a user while the ray-sum image is displayed, and specifies a distance in accordance with a physical shape of the subject based on the positions of the two points.

7. The dose calculation apparatus according to claim 1, wherein the value representing X-ray intensity during taking of medical images is a CTDIvol.

8. A method for controlling a dose calculation apparatus comprising steps of:
generating a ray-sum image from a plurality of medical images acquired by imaging a subject with an X-ray computed tomography (CT) apparatus;
specifying physical shape information of at least one of body width and body thickness of the subject using the ray-sum image generated in the generating step;
acquiring a correction coefficient corresponding to the physical shape information of at least one of the body width and the body thickness specified in the specifying step from a storage unit configured to store a relationship between the physical shape information and the correction coefficient; and
calculating dose in accordance with a physical shape of the subject based on the correction coefficient acquired in the acquiring step and dose information acquired by taking of medical images.

9. A non-transitory recording medium storing a program including a plurality of instructions that, when executed, cause at least one computer to execute a method, the method comprising:
generating a ray-sum image from a plurality of medical images acquired by imaging a subject with an X-ray computed tomography (CT) apparatus;
specifying physical shape information of at least one of a body width and a body thickness of the subject using the generated ray-sum image;
acquiring a correction coefficient corresponding to the specified physical shape information of at least one of the body width and the body thickness from a storage unit configured to store a relationship between the physical shape information and the correction coefficient; and
calculating dose in accordance with a physical shape of the subject based on the acquired correction coefficient and dose information acquired by taking of medical images.

10. A dose management system including a dose calculation apparatus and a server apparatus, the dose management system comprising:
- a specifying unit configured to specify physical shape information including at least one of a body width and a body thickness of a subject using a ray-sum image generated from a plurality of medical images acquired by imaging the subject with an X-ray computed tomography (CT) apparatus;
- an acquisition unit configured to acquire a correction coefficient corresponding to the physical shape information specified by the specifying unit from a storage unit configured to store a relationship between the physical shape information and the correction coefficient; and
- a calculation unit configured to calculate dose in accordance with a physical shape of the subject based on the correction coefficient acquired by the acquisition unit and dose information acquired by taking of medical images.

11. The dose management system according to claim 10, further comprising a storage unit configured to store the dose calculated by the calculation unit together with the physical shape information.

12. The dose management system according to claim 11, wherein the specifying unit, the acquisition unit, and the calculation unit are provided in the dose calculation apparatus and the storage unit is provided in the server apparatus.

13. The dose management system according to claim 12, wherein the server apparatus further includes a graph generating unit configured to generate a dose management graph corresponding to predetermined conditions based on the dose stored in the storage unit.

14. A method for controlling a dose management system including a dose calculation apparatus and a server apparatus, comprising steps of:
- generating a ray-sum image from a plurality of medical images acquired by imaging a subject with an X-ray computed tomography (CT) apparatus;
- specifying physical shape information of at least one of body width and body thickness of the subject using the ray-sum image generated in the generating step;
- acquiring a correction coefficient corresponding to the physical shape information specified in the specifying step from a storage unit configured to store a relationship between the physical shape information and the correction coefficient; and
- calculating dose in accordance with a physical shape of the subject based on the correction coefficient acquired in the acquiring step and dose information acquired by taking of medical images.

15. A non-transitory recording medium storing a program including a plurality of instructions that, when executed, cause at least one computer to execute a method, the method comprising:
- generating a ray-sum image from a plurality of medical images acquired by imaging a subject with an X-ray computed tomography (CT) apparatus;
- specifying physical shape information of at least one of body width and body thickness of the subject using the generated ray-sum image;
- acquire a correction coefficient corresponding to the specified physical shape information from a storage unit configured to store a relationship between the physical shape information and the correction coefficient; and
- calculate dose in accordance with a physical shape of the subject based on the acquired correction coefficient and dose information acquired by taking of medical images.

* * * * *